US012662506B2

(12) United States Patent
Chen et al.

(10) Patent No.: US 12,662,506 B2
(45) Date of Patent: Jun. 23, 2026

(54) SYNTHESIS METHOD FOR SELAMECTIN

(71) Applicants: ZHEJIANG RONGYAO BIOTECH CO., LTD., Taizhou (CN); ZHEJIANG UNIVERSITY, Hangzhou (CN)

(72) Inventors: Rener Chen, Taizhou (CN); Xiuwen Zhong, Hangzhou (CN); Youchun Huang, Hangzhou (CN); Lei Zhang, Hangzhou (CN); Wenteng Chen, Hangzhou (CN); Yongping Yu, Hangzhou (CN)

(73) Assignees: ZHEJIANG RONGYAO BIOTECH CO., LTD., Taizhou (CN); ZHEJIANG UNIVERSITY, Hangzhou (CN)

( * ) Notice: Subject to any disclaimer, the term of this patent is extended or adjusted under 35 U.S.C. 154(b) by 511 days.

(21) Appl. No.: 18/303,592

(22) Filed: Apr. 20, 2023

(65) Prior Publication Data

US 2023/0257411 A1 Aug. 17, 2023

Related U.S. Application Data

(63) Continuation of application No. PCT/CN2022/092181, filed on May 11, 2022.

(30) Foreign Application Priority Data

Nov. 11, 2021 (CN) ......................... 202111330352.X

(51) Int. Cl.
*C07H 17/08* (2006.01)
*C07H 1/00* (2006.01)

(52) U.S. Cl.
CPC ............... *C07H 17/08* (2013.01); *C07H 1/00* (2013.01)

(58) Field of Classification Search
CPC .................................. C07H 17/08; C07H 1/00
See application file for complete search history.

(56) References Cited

U.S. PATENT DOCUMENTS 6,605,595 B1 * 8/2003 Omura ............... A61K 31/7048 549/264

FOREIGN PATENT DOCUMENTS

| | | | | | |
|---|---|---|---|---|---|
| CN | 1099394 | A | | 3/1995 | |
| CN | 1266437 | A | | 9/2000 | |
| CN | 103360444 | A | | 10/2013 | |
| CN | 107021990 | A | | 8/2017 | |
| CN | 107118247 | A | | 9/2017 | |
| CN | 108707173 | A | | 10/2018 | |
| CN | 111116692 | A | * | 5/2020 | ............... C07H 1/00 |
| CN | 114106071 | A | | 3/2022 | |
| WO | 2017055502 | A1 | | 4/2017 | |

OTHER PUBLICATIONS

First Office Action(CN202111330352.X); Date of Mailing: Jul. 13, 2023.

Avermectins-and-Flea-Control: Structure-Activity-Relationships-and-the-Selection-of-Selamectin-for-Development-as-an-Endectocide-for-Companion-Animals.

International Search Report (PCT/CN2022/092181); Date of Mailing: Aug. 3, 2022.

* cited by examiner

*Primary Examiner* — Bahar Craigo

(74) *Attorney, Agent, or Firm* — Wiersch Law Group

(57) ABSTRACT

A synthesis method for selamectin was developed, where doramectin is oxidized by manganese dioxide, oximated and de-sugared in one-step by an aqueous solution of hydroxylamine hydrochloride, and then selectively reduced in the presence of Wilkinson's catalyst and hydrogen to obtain selamectin. Doramectin is oxidized to a carbonyl group firstly, so that the generation of impurities during the subsequent reaction is reduced; t-butyl alcohol with a larger steric hindrance is used as a solvent, so that transesterification impurities are avoided; the hydrogenation is implemented in the final step, and the crude product is recrystallized before the hydrogenation reaction, so that the cost is greatly reduced. The method of the present application with an overall yield of 57%. The purity of product was 97.11%. All impurities meet the requirements of Pharmacopoeia. The present application is a simpler, more economical and more efficient synthesis method, and is suitable for industrial production.

8 Claims, 1 Drawing Sheet

SYNTHESIS METHOD FOR SELAMECTIN

CROSS-REFERENCE TO RELATED APPLICATIONS

The present application is a National Stage of International Application No. PCT/CN2022/092181, filed on May 11, 2022, which claims priority to Chinese Patent Application No. 202111330352.X, filed on Nov. 11, 2021, both of which are hereby incorporated by reference in their entireties.

TECHNICAL FIELD

The present application belongs to the technical field of drug synthesis and relates to a synthesis method for avermectins, in particular to a synthesis method for selamectin.

BACKGROUND

Avermectins, which are a group of macrocyclic lactones produced by fermentation of *Streptomyces*, are currently the most widely used class of potent broad-spectrum antiparasitic agents, among which drugs that have been commercialized include avermectin (AVM), ivermectin (IVM), doramectin (DRM), eplinomycin (EPR), and selamectin (SEI), etc.

Selamectin is an avermectin antibiotic fermented by a genetically recombined new strain of *Streptomyces sav ermitilis*, developed by Pfizer Inc., USA, obtained by chemically synthesizing structural modifications of doramectin, first marketed in the United Kingdom in July 1999 under the trade name Revolution. Selamectin exhibits broad inhibitory and killing effects against many parasites, including fleas, scabies, ticks, hookworms, lice, nematodes, and heartworms, etc., is superior to other avermectins in the treatment of fleas (*Ctenocephalides felis* and *canis*), mites, ticks, and some in vivo nematodes (roundworms and hookworms) infections in dogs and cats and are a marketed pet antiparasitic drug.

Selamectin is chemically named 25-cyclohexanyl-25-de (1-methylpropyl)-5-deoxy-22, 23-dihydro-5-(oximino)-avermectin B1 monosaccharide, differs most from other avermectin antibiotics in that the substituent at position C5 is oximino. It has a molecular weight of 769.44 and is a white or yellowish crystalline powder with the following structural formula:

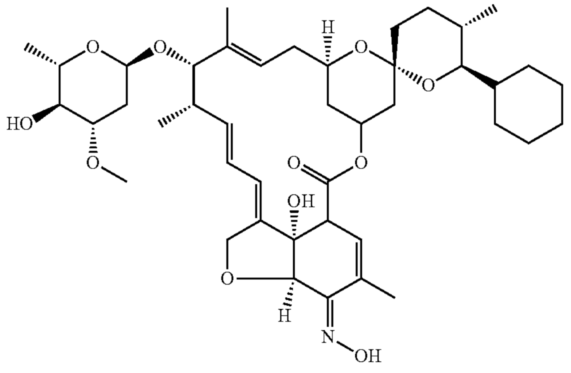 [SMILES: CO[C@H]1C[C@H](O[C@@H]2/C(C)=C/C[C@@H]3CC(C[C@]4(CC[C@H](C)[C@@H](C5CCCCC5)O4)O3)OC(=O)C3C=C(C)/C(=N\O)[C@H]4OC/C(=C\C=C\[C@@H]2C)[C@@]34O)O[C@@H](C)[C@@H]1O]

Selamectin

The synthetic process of selamectin has been improved over the last two decades, and the route used by most domestic manufacturers is the U.S. Pat. No. 5,981,500 by Pfizer Corporation. The overall route is to obtain selamectin by hydrogenation, desugarization, oxidation and oximation of doramectin in four steps.

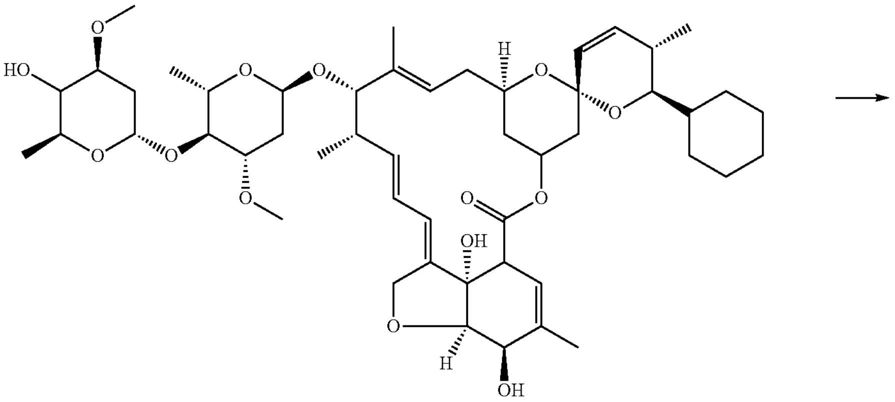

-continued

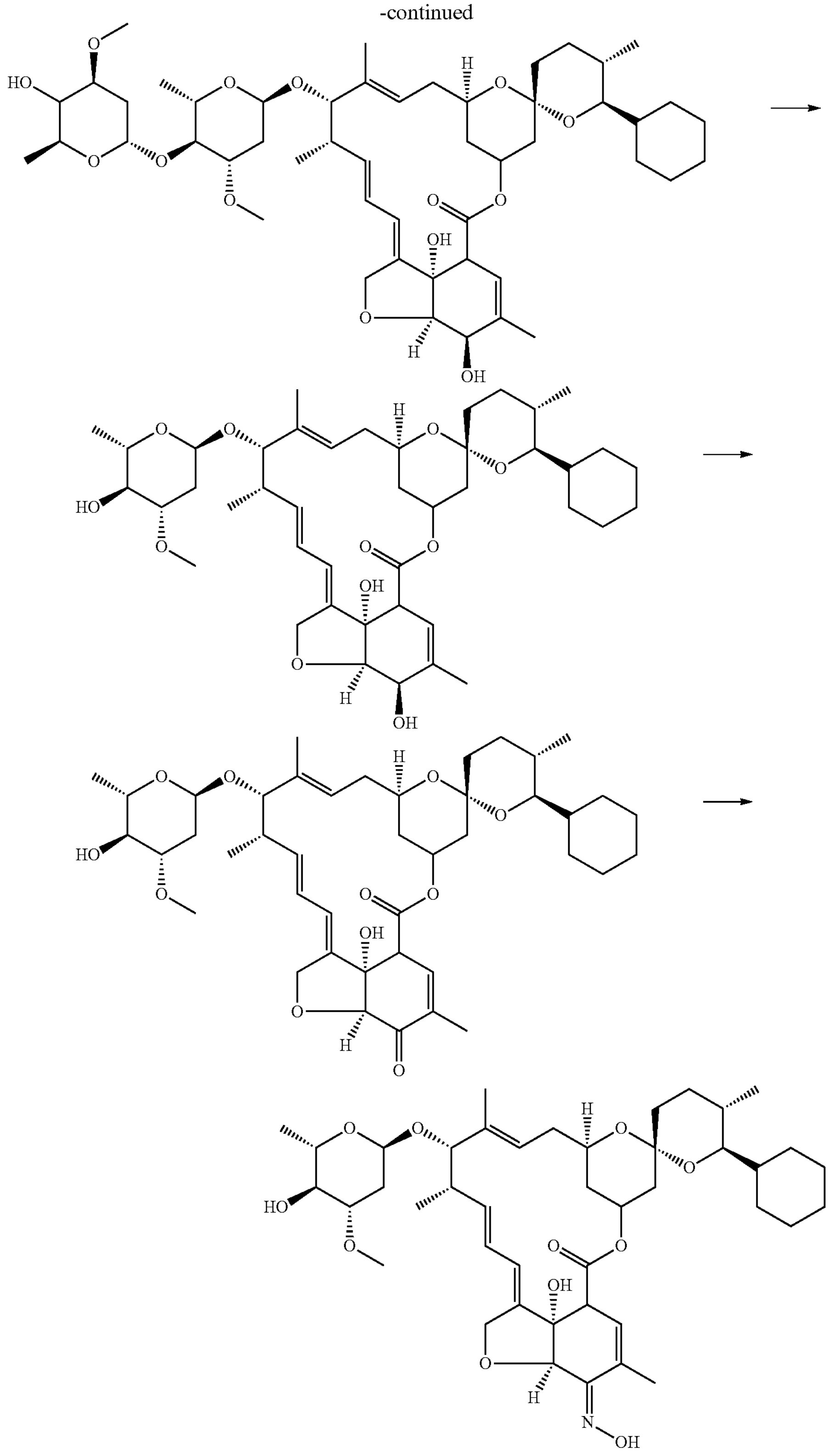

Starting from doramectin, the first step is to reduce the double bonds at C-22, 23 positions to single bonds in the presence of Wilkinson's catalyst. In the second step, a desugaring reaction is carried out in an isopropyl sulfate solution to hydrolytically remove one molecule of sugar. The third step is to oxidize the hydroxyl group at the C-5 position of the de-sugared intermediate to a ketone oxidized by activated manganese dioxide. The fourth step is to oximate the carbonyl group at C-5 using hydroxylamine hydrochloride to give selamectin. The amount of the Wilkinson's catalyst used in the first hydrogenation reaction of this patent is as high as 93% w/w, but the price of precious metal catalysts have risen in recent years, which leads to high process costs, and each intermediate needs silica gel chromatography separation, so the post-treatment operation is complicated. The entire route produces selamectin with low purity, low yield, high cost, and is not conducive to commercial production.

U.S. Pat. No. 6,906,184 discloses a modified selamectin synthesis method by Pfizer. The new process involves hydrogenation, oxidation, desugarization and oximation, wherein desugarization and oximation are accomplished in one-step.

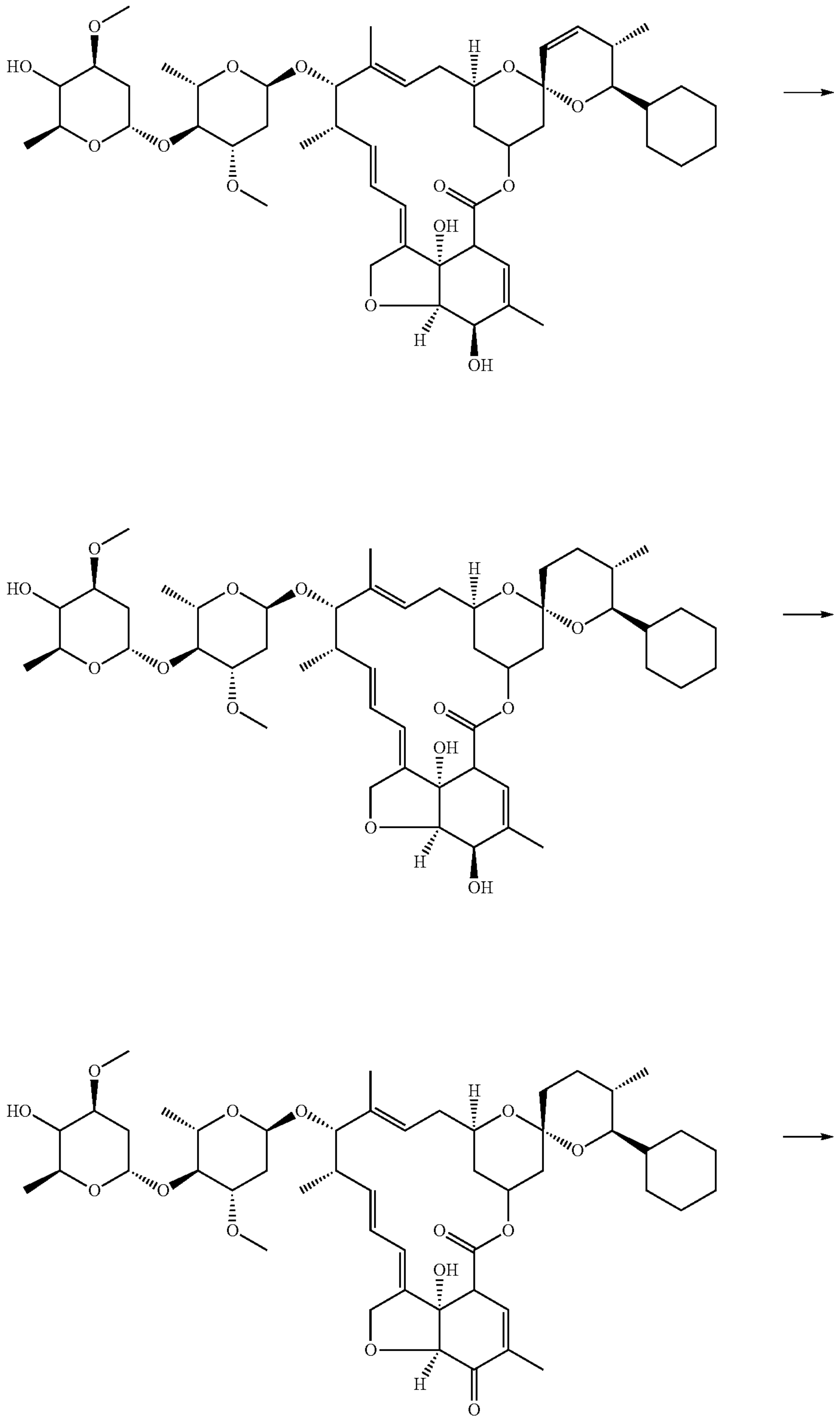

-continued

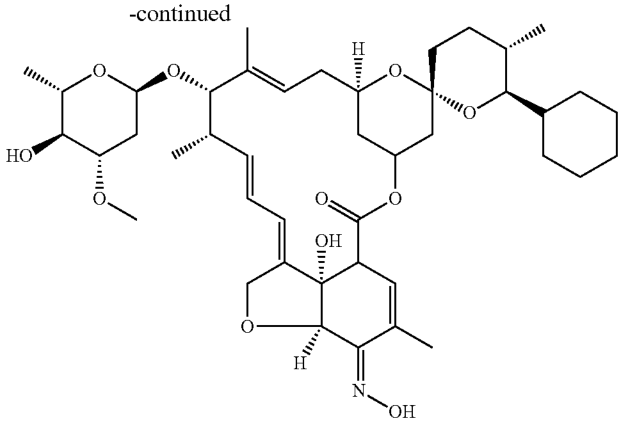

First, the double bond at C-22, 23 positions of doramectin is reduced to single bond, then the hydroxyl group at C-5 position is oxidized to a ketone, followed by reaction with hydroxylamine hydrochloride for simultaneous desugarization hydrolysis and oximation. This patent, while simplifying the process steps, reducing work-up operations and separation steps, still fails to solve the problem of low yields, with only 35% yield for the entire route.

WO 2017055502 discloses a synthetic route to selamectin from doramectin in four steps of desugarization oxidization, hydrogenation and oximation.

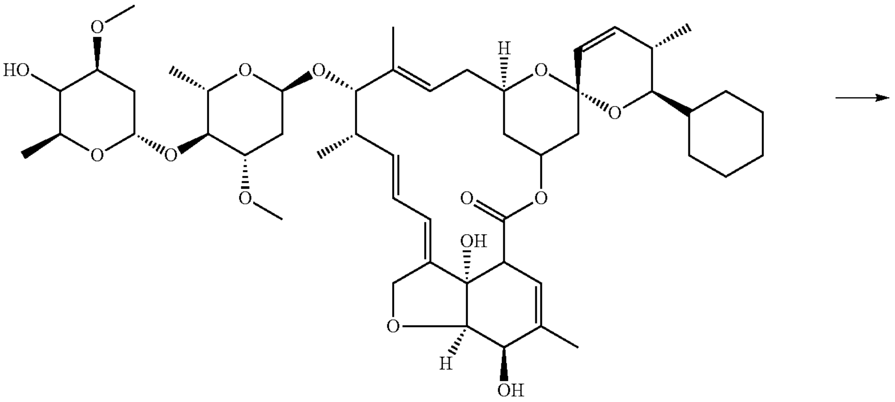

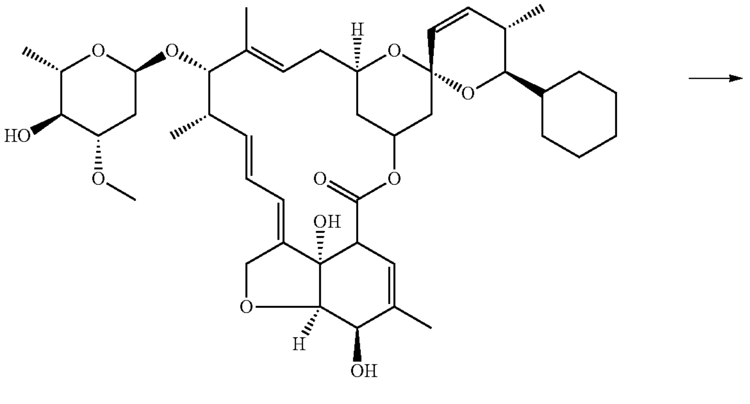

-continued

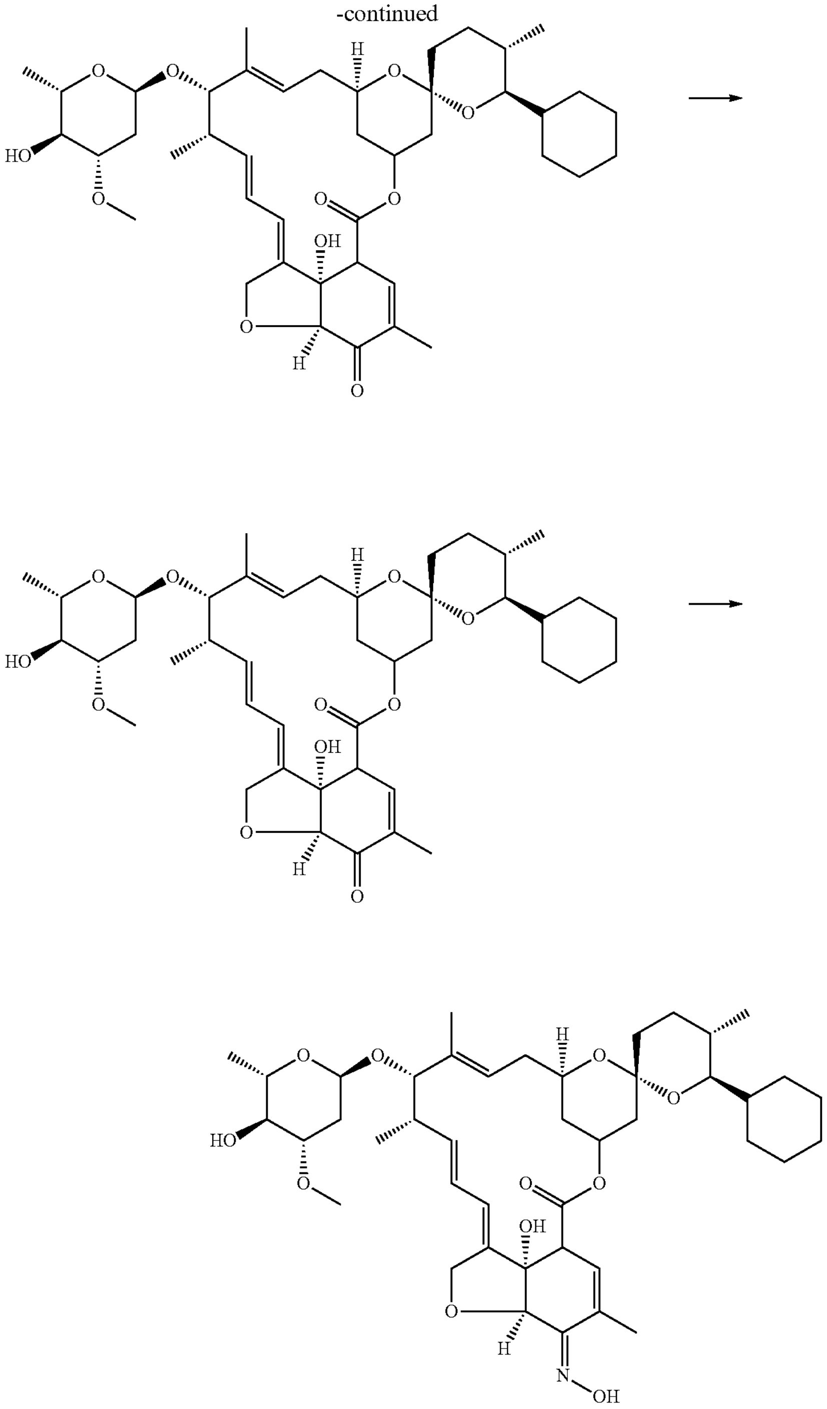

Doramectin is first subjected to sulfuric acid to remove one sugar molecule in a mixed solvent of acetonitrile and water. The second step is to oxidize the hydroxyl group at C-5 of the desugared intermediate to a ketone using DMP as an oxidizing agent. The third step is to reduce the double bond at the C-22, 23 positions to single bond under catalysis of the Wilkinson's catalyst. Final oximation of the carbonyl group at C-5 via hydroxylamine hydrochloride gives selamectin. This process uses DMP as an oxidizing agent, the reaction solution is washed sequentially with sodium thiosulfate, hydrochloric acid, sodium hydroxide and saturated brine, and the post-treatment is complicated, time-consuming, and inefficient. The reaction system also uses a relatively large number of solvents, including high boiling solvents such as 1, 4-dioxane.

In summary, the prior art patented technology suffers from a number of shortcomings, such as low yield, high cost, tedious work-up operations and separation steps.

SUMMARY

It is an object of the present application to provide a synthesis method for selamectin in the following route:

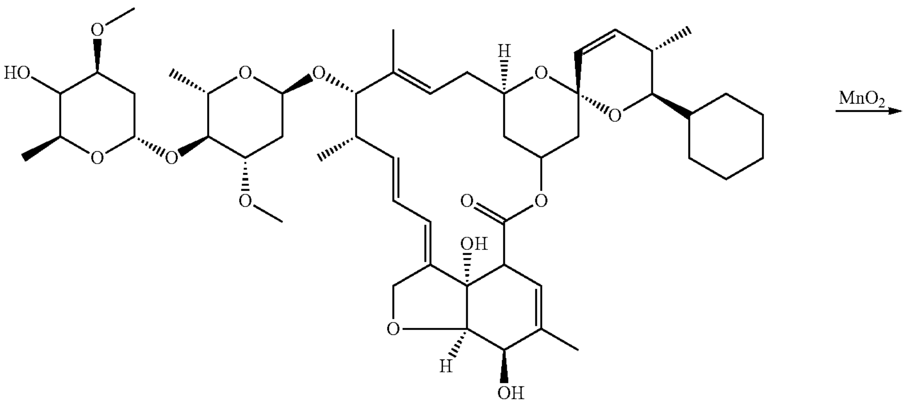
A
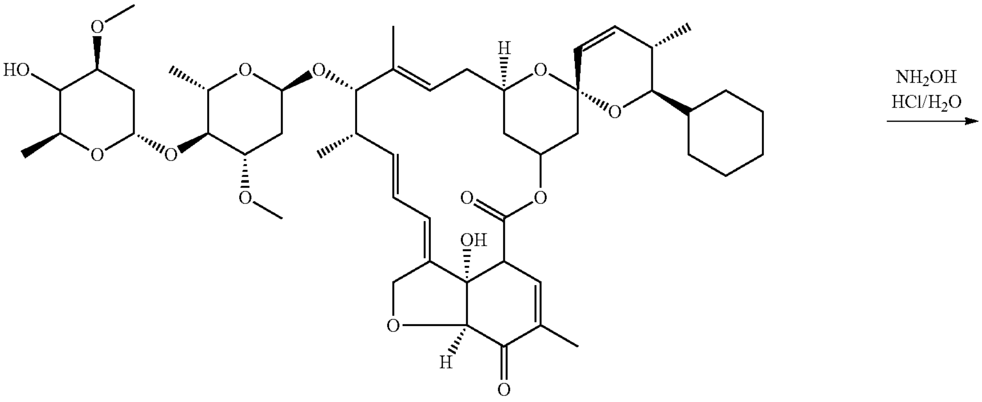
B
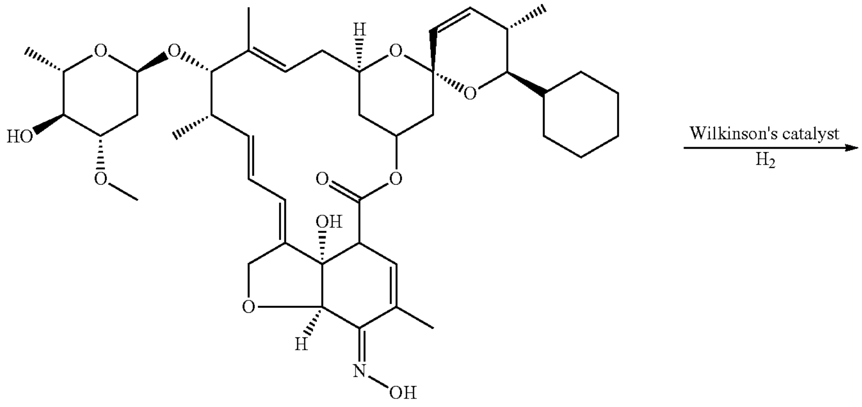
C

-continued

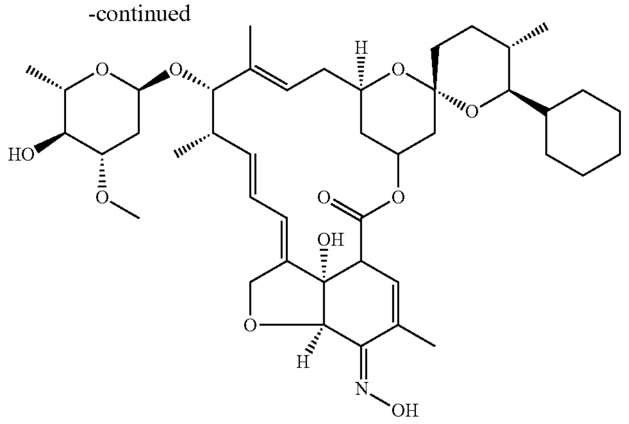

D

In particular, the method is implemented by the following steps:

(1) reacting doramectin A in the presence of manganese dioxide ($MnO_2$) at room temperature (20-30° C.) for 7-14 hours, removing the manganese dioxide by suction filtration after reaction, and removing the solvent under reduced pressure to obtain an oxidized intermediate B;

(2) dissolving the intermediate B in a protic solvent, adding an aqueous solution of hydroxylamine hydrochloride dropwise, and carrying out the desugaroximation reaction at 26-35° C. for 35-48 hours; after the reaction, neutralizing with sodium carbonate or sodium bicarbonate, and removing the solvent under reduced pressure to obtain a yellow solid; adding the salt in the aqueous solution, and recrystallizing by a mixed solvent of acetonitrile and water to obtain an oximated and desugared intermediate C in one-step; and (3) introducing 3-4 bar hydrogen, and reacting the intermediate C in the presence of 4-8% w/w Wilkinson's catalyst at 30° C. for 8 hours to give selamectin D after toluene recrystallization.

where, in the step (2), the protic solvent may be a solution of methanol, ethanol, isopropanol, tert-butyl alcohol, or any mixture thereof, preferably tert-butyl alcohol.

In step (2), the desugarization oximation reaction temperature is 26-35° C., preferably 30-32° C.

In step (2), the weight ratio of the intermediate C to the mixed solvent is 1:2 to 1:4, preferably 1:3, where the weight ratio of water to acetonitrile in the mixed solvent is 1:2 to 1:4, preferably 1:2.

The method for recrystallization purification in step (2) is as follows: adding the mixed solvent of acetonitrile and water to the crude product C, keeping the temperature at 40-80° C. and stirring for 2 hours, cooling and precipitating, carrying out suction filtration, washing the solid with the mixed solvent until white, and drying the filter cake.

In step (3), the weight ratio of the crude selamectin D to toluene is 1:2 to 1:5, preferably 1:4.

The method for recrystallization purification in step (3) is as follows: adding toluene to the crude selamectin D, dissolving at an elevated temperature, keeping the temperature 40-80° C. and stirring for 2 hours, cooling and precipitating, carrying out suction filtration, washing the solid with toluene until white, and drying the filter cake.

The present application makes route and process innovations over the prior art and provides a more simple, economical and efficient synthesis. The present application provides a synthesis method for selamectin which is more simple, economical and efficient, has high raw material utilization and high yield, shortens the production cycle, also saves the cost of solvents, and is suitable for industrial production. The main innovations of the present application compared to the prior art are listed as follows:

(1) The hydroxyl group at the C-5 position of the starting doramectin is first oxidized to a carbonyl group to reduce the generation of impurities during the subsequent reaction.

(2) The desugarization and oximation reaction of the oxidized intermediate B uses t-butyl alcohol with a larger steric hindrance as a solvent, so that transesterification impurities generated when methanol or isopropanol are used as a solvent are avoided.

(3) In recent years precious metal prices have risen, the hydrogenation is put in the last step and the crude product is purified before hydrogenation, so that the consumption of the catalyst (4-8% w/w) is saved, and the cost is greatly reduced.

(4) The yield of the new process is up to 57%. Pure selamectin was analyzed by HPLC quality and had a purity of 97.11%, with each known and unknown impurity meeting pharmacopoeia requirements.

DESCRIPTION OF EMBODIMENTS

Figure 1:
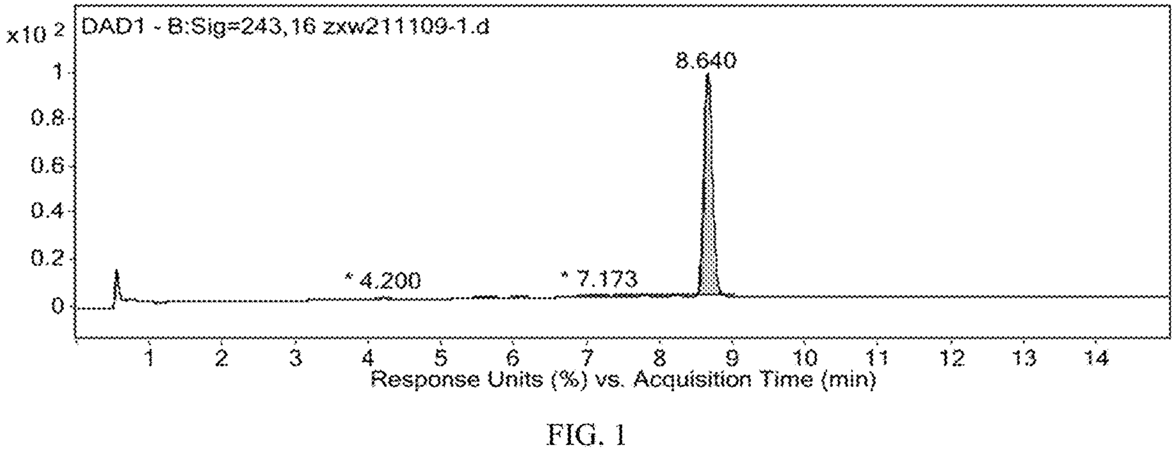
FIG. 1 is a LC-MS spectrogram of pure selamectin.

The summary will be further explained and illustrated below with reference to specific examples, which are not to be construed as limiting or limiting the scope of the application.

Example 1 Oxidation Reaction

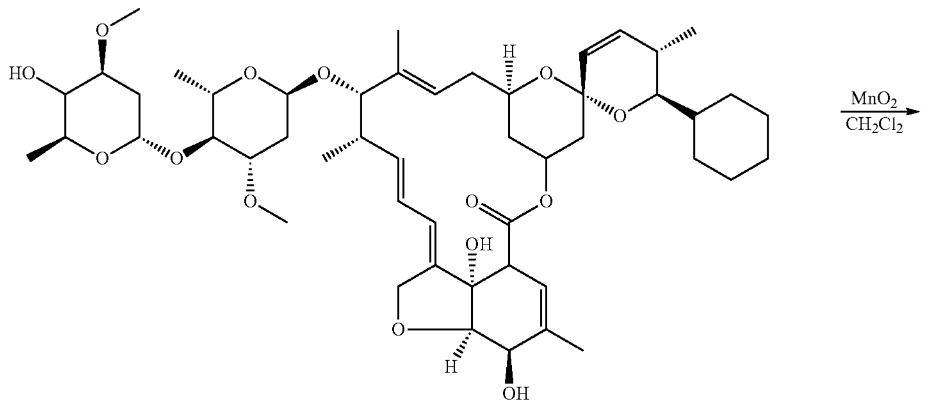

A

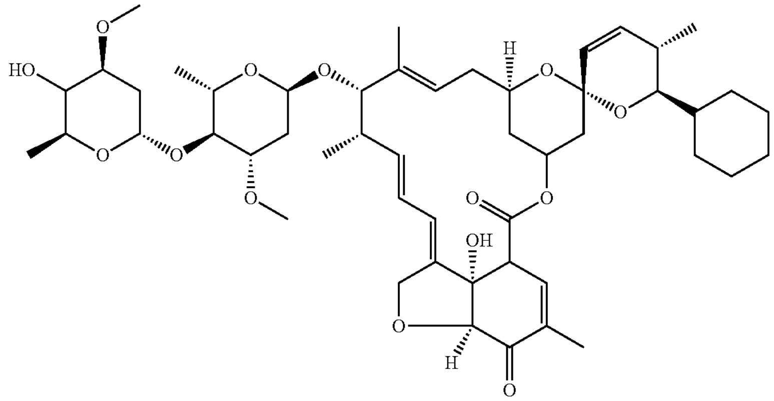

B 500 mL of dichloromethane was added to a three-neck flask, 100 g of doramectin A was weighed into the three-neck flask in one portion via an addition funnel; after stirring to dissolve the reactants, another 200 g of manganese dioxide was added, and the reaction was carried out at room temperature (20-30° C.) for 8 h; the reaction was monitored by LC-MS, and reaction could be processed after the reaction of the starting material; the product had a purity of 97.65% by LC-MS. After the reaction the manganese dioxide was removed by suction filtration and the filtrate was stripped of solvent under reduced pressure in a water bath at 45° C. to give a pale yellow solid which was dried in an oven at 45° C. to a constant weight to give 98.96 g of an intermediate B with a yield of 99%.

Example 2 Desugarization, Oximation Reaction

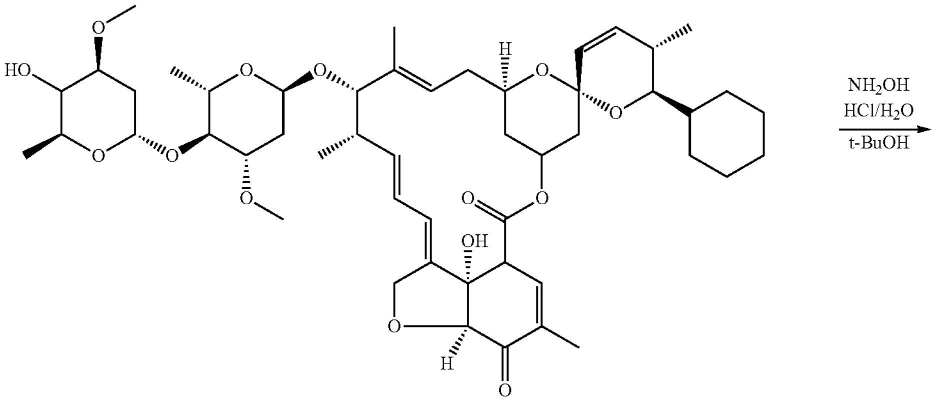

B

-continued

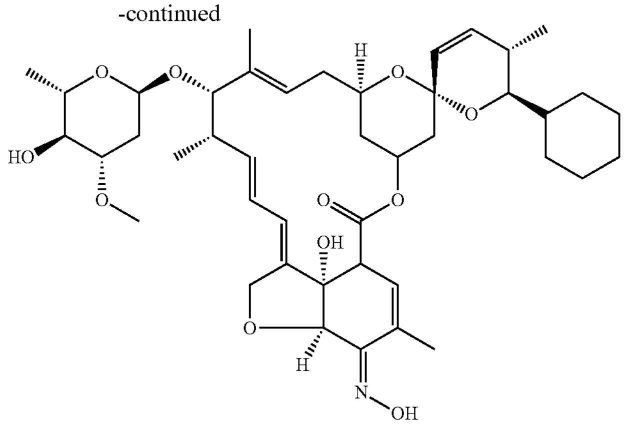

C 600 mL of tert-butyl alcohol and 100 g of the intermediate B were added to a three-necked flask, and the solution was stirred clear at room temperature; 19 g of hydroxylamine hydrochloride was dissolved in 30 mL of water; after the solution was clear, an aqueous solution of hydroxylamine hydrochloride was slowly added dropwise to the system; the reaction was carried out at 26-35° C. for 35-48 hours; the reaction was monitored by LC-MS; the reaction was stopped when 10-12% of the starting material B remained. The LC-MS purity of a product C was 80%.

15 g of sodium carbonate was dissolved in 50 mL of water, and after the solution was clear, it was slowly added dropwise to the system; the solvent was removed under reduced pressure in a water bath at 50° C. to give a yellow solid; 500 mL of water was added, the solution was stirred at room temperature for 2 h and then subjected to suction filtration; the filter cake was placed in an oven at 50° C., dried and weighed to obtain a solid of 89.33 g, with a yield of 104%.

Example 3 Desugarization, Oximation Reaction

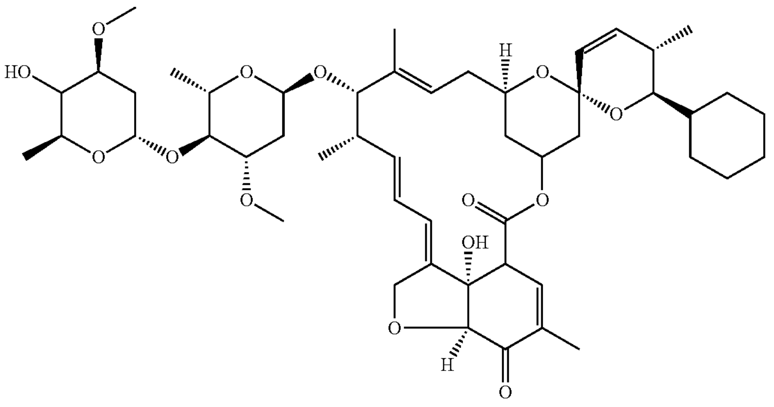

B

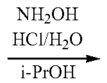

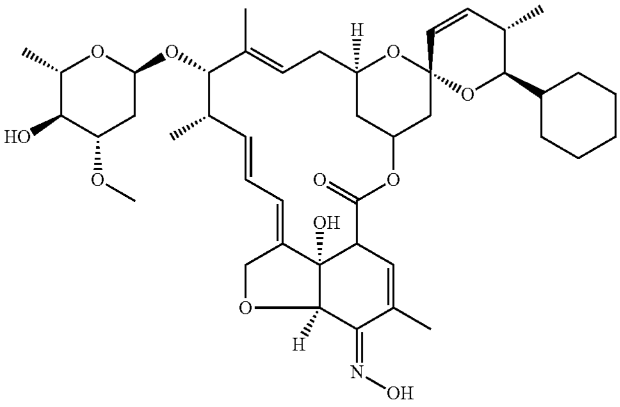 [SMILES: CO[C@H]1C[C@H](O[C@@H]2/C(C)=C/C[C@@H]3CC(C[C@]4(CC[C@H](C)[C@@H](C5CCCCC5)O4)O3)OC(=O)C3C=C(C)/C(=N\O)[C@H]4OC/C(=C\C=C\[C@@H]2C)[C@@]34O)O[C@@H](C)[C@@H]1O]

C 500 mL of isopropanol was added and 100 g of the intermediate B were added to a three-neck flask, and the solution was stirred clear at room temperature; 19 g of hydroxylamine hydrochloride was dissolved in 30 mL of water; after the solution was clear, an aqueous solution of hydroxylamine hydrochloride was slowly added dropwise to the system; the reaction was carried out at 26-35° C. for 35-48 hours; the reaction was monitored by LC-MS; the reaction was stopped when 10-12% of starting material B remained; the LC-MS purity of the product C was 76%.

15 g of sodium carbonate was dissolved in 50 mL of water; after the solution was clear, it was slowly added dropwise to the system; the solvent was removed under reduced pressure in a water bath at 50° C. to give a yellow solid; 500 mL of water was added, the solution was stirred at room temperature for 2 h and then subjected to suction filtration; the filter cake was placed in an oven at 50° C., dried and weighed to obtain a solid of 88.17 g, with a yield of 103%.

Example 4 Desugarization, Oximation Reaction

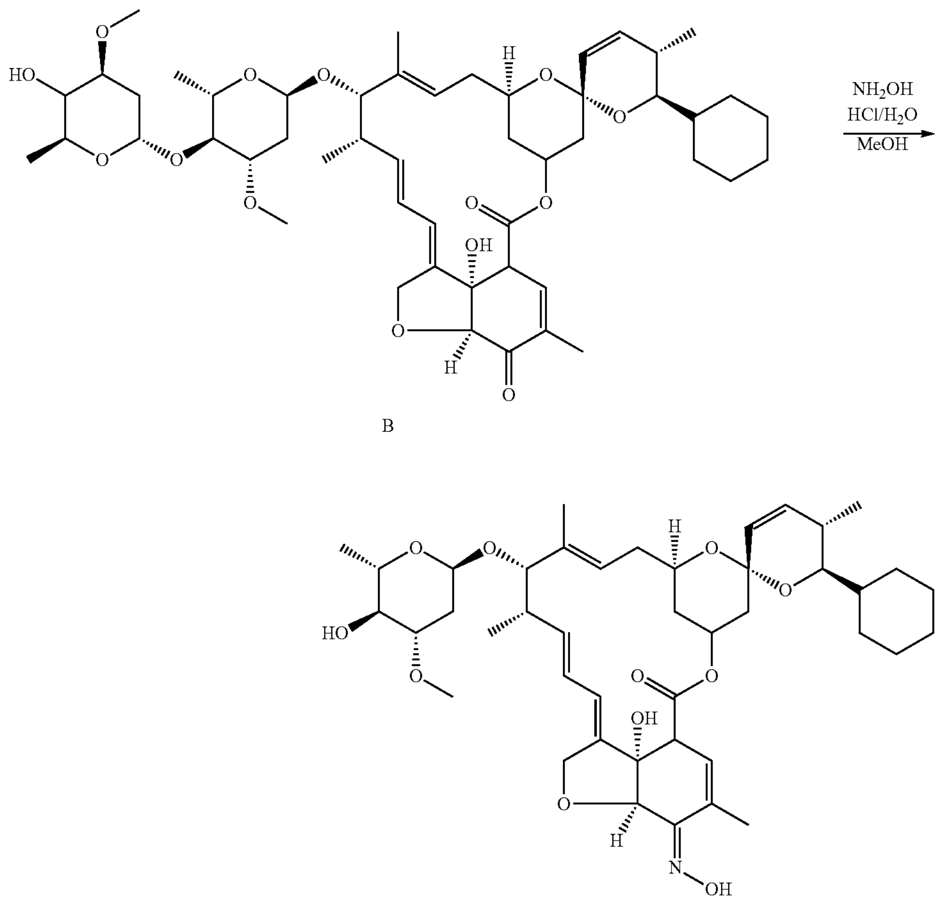

B

C 350 mL of methanol was added to a three-necked flask and 100 g of the intermediate B was added portionwise; the solution was stirred clear at room temperature; 19 g of hydroxylamine hydrochloride was dissolved in 30 mL of water, and after the solution was clear, an aqueous solution of hydroxylamine hydrochloride was slowly added dropwise to the system; the reaction was carried out at room temperature (20-25° C.) for 12-18 hours; the reaction was monitored by LC-MS; the reaction was stopped when the starting material was <5%; the LC-MS purity of the product C was 75%.

15 g of sodium carbonate was dissolved in 50 mL of water; after the solution was clear, it was slowly added dropwise to the system; the solvent was removed under reduced pressure in a water bath at 50° C. to give a yellow solid; 500 mL of water was added, the solution was stirred at room temperature for 2 h and then subjected to suction filtration; the filter cake was placed in an oven at 50° C., dried and weighed to obtain a solid of 86.88 g, with a yield of 102%.

Example 5 Refinement of Intermediate C 90 mL of acetonitrile was added to a three-necked flask, and then was heated to bring the internal temperature of the solvent to 60° C.; 45 g of crude C was added and dissolved by stirring, 45 mL of water was added and a solid was precipitated; after stirring at 60° C. for 2 h, heating was stopped followed by cooling crystallization; suction filtration was carried out, the filter cake was washed with a mixed solvent of acetonitrile and water to white, and then was placed in 50° C. oven; the filter cake was weighed 26.17 g after oven drying, with a yield of 61% and a LC-MS purity of 95.51%.

Example 6 Hydrogenation

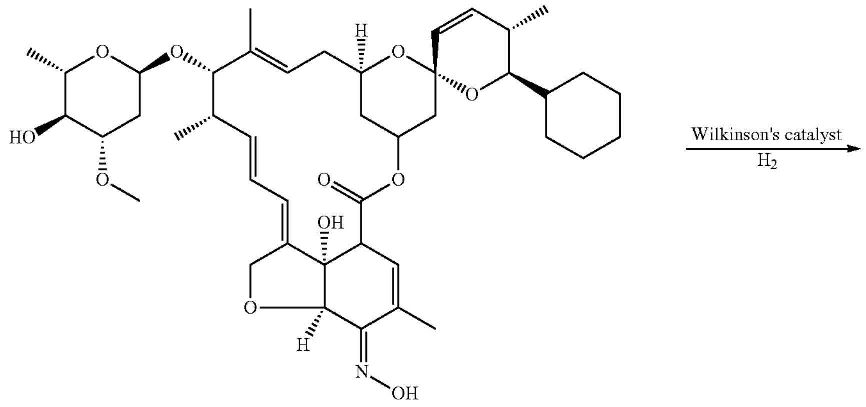

C

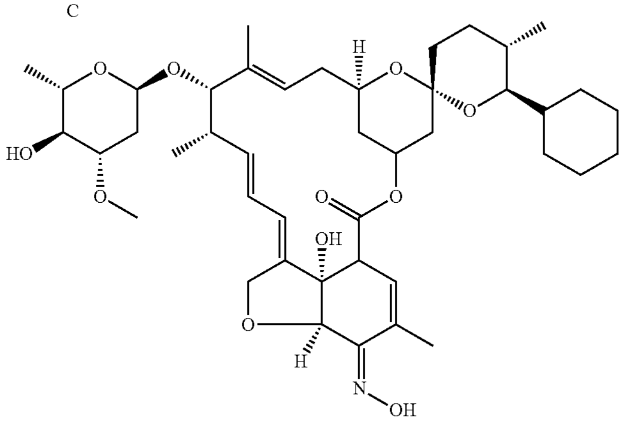

D 35 mL of acetone was added to an reaction vessel, 7 g of purified intermediate C was weighed into the reaction vessel, and after stirring to make the solution clear, 0.42 g of the Wilkinson's catalyst was added; the reaction vessel was sealed and 3-4 bar hydrogen gas was introduced to perform 3 replacements; it was set that the reaction was started at 30° C.; the reaction was monitored by LC-MS after 8 h; the starting material was completely reacted and a product D had a LC-MS purity of 96.88%; 0.35 g of activated carbon (5% w/w) was added to the reaction mixture; the reaction mixture was continuously stirred at 30° C. for 1 h, and was subjected to suction filtration; the filtrate was spin-dried under reduced pressure in a water bath temperature of 50° C. and oven-dried to a constant weight at 50° C. to give 7 g of a brown solid.

Example 7 Refinement of D 28 mL of toluene was added to a three-necked flask and heated to an internal temperature of 60° C.; 7 g of crude selamectin was added to the flask through an addition funnel and the solution was stirred to clear; after stirring at 60° C. for 2 h, the heating was turned off and the mixture was allowed to cool to precipitate; suction filtration was carried out, the filter cake was washed with 28 mL of toluene, and the filter cake was oven-dried to a constant weight at 50° C. to give 6.28 g of selamectin as a white solid, with a recovery of 90% and a LC-MS purity of 97.21%; the results are shown in Table 1 and FIG. 1.

TABLE 1

| Peak # | Retention Time | Peak Area | Peak Height | Peak Area % |
|---|---|---|---|---|
| 1 | 4.2 | 70.04 | 13.27 | 0.56 |
| 2 | 5.787 | 10.17 | 0 | 0.08 |
| 3 | 6.073 | 39.44 | 7.54 | 0.32 |
| 4 | 7.173 | 45.9 | 5.31 | 0.37 |
| 5 | 7.56 | 18.91 | 2.01 | 0.15 |
| 6 | 7.78 | 80.81 | 11.06 | 0.65 |
| 7 | 8.213 | 83.26 | 11.93 | 0.67 |
| 8 | 8.64 | 12121.31 | 1537.25 | 97.21 |
| Total | | 12469.84 | 1588.37 | 100 |

Figure 2:
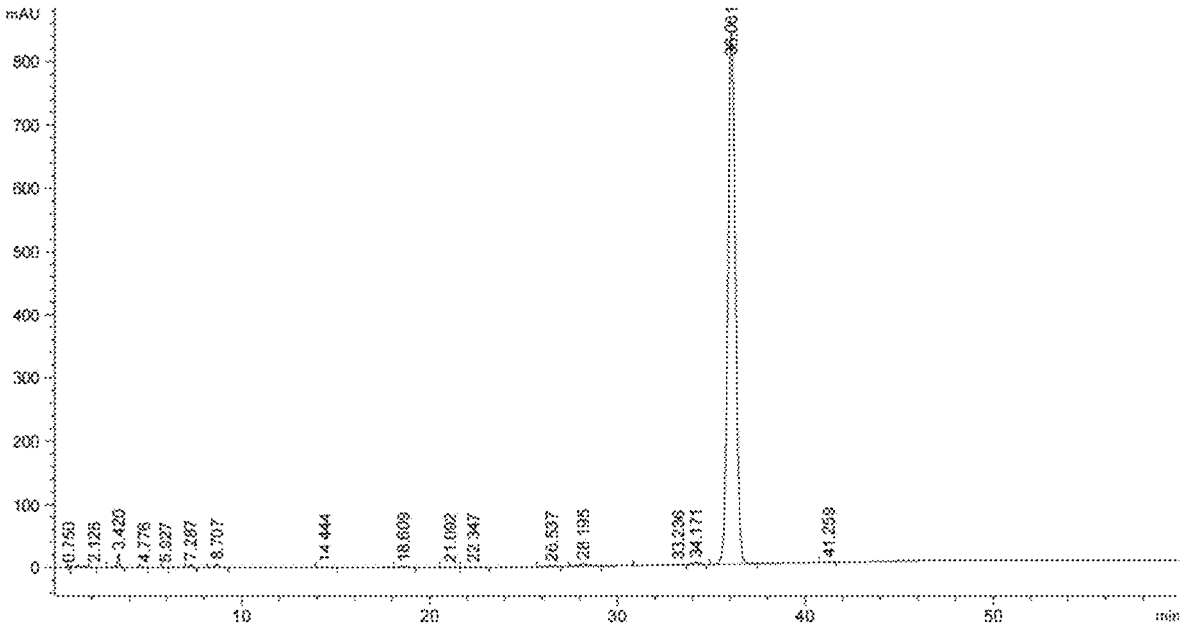
FIG. 2 is a HPLC spectrogram of pure selamectin.

The new process developed in the present application has a higher yield with an overall yield of 57%. HPLC quality analysis was carried out for the selamectin pure product, and the purity was 97.11%. The results are shown in Table 2 and FIG. 2, with each known and unknown impurity meeting the pharmacopoeia requirements.

TABLE 2

| Peak # | Retention Time | Peak Area | Peak Height | Peak Area % |
|---|---|---|---|---|
| 1 | 0.750 | 17.08073 | 2.22989 | 0.0705 |
| 2 | 2.128 | 5.15401 | 6.24402e−1 | 0.0213 |
| 3 | 3.420 | 163.95235 | 20.79733 | 0.6770 |
| 4 | 4.776 | 3.18470 | 3.20375e−1 | 0.0132 |
| 5 | 5.927 | 4.46985 | 4.45214e−1 | 0.0185 |

TABLE 2-continued

| Peak # | Retention Time | Peak Area | Peak Height | Peak Area % |
|---|---|---|---|---|
| 6 | 7.287 | 42.12532 | 3.64840 | 0.1739 |
| 7 | 8.707 | 82.76653 | 5.01769 | 0.3418 |
| 8 | 14.444 | 10.56633 | 3.68682e−1 | 0.0436 |
| 9 | 18.609 | 34.40981 | 1.14684 | 0.1421 |
| 10 | 21.092 | 12.59899 | 3.94243 | 0.0520 |
| 11 | 22.347 | 22.86115 | 5.60881e−1 | 0.0944 |
| 12 | 26.537 | 25.81116 | 8.26434 | 0.1066 |
| 13 | 28.195 | 131.01105 | 3.50173 | 0.5410 |
| 14 | 33.236 | 31.93697 | 5.32464e−1 | 0.1319 |
| 15 | 34.171 | 124.82230 | 3.48557 | 0.3835 |
| 16 | 36.061 | 2.35185e4 | 841.05994 | 97.1138 |
| 17 | 41.259 | 18.13955 | 7.57931e−1 | 0.0749 |
| Total | | 2.42174e4 | 885.71801 | 100 |

What is claimed is:

1. A synthesis method for selamectin, the method comprising the following steps of:

(1) reacting doramectin A with manganese dioxide at 20-30° C. for 7-14 hours to give an oxidized intermediate B;

(2) dissolving the intermediate B in tert-butyl alcohol, adding dropwise an aqueous solution of hydroxylamine hydrochloride, and reacting at 26-35° C. for 35-48 hours; neutralizing with sodium carbonate or sodium bicarbonate after the reaction, and removing the solvent under reduced pressure to obtain a yellow solid; dissolving any formed salts and residual hydroxylamine by adding water to the yellow solid, followed by suction filtration to give a yellow filter cake, and recrystallizing the yellow filter cake from a mixed solvent of acetonitrile and water to obtain an oximated and de-sugared intermediate C in one-step; and (3) introducing hydrogen at 3-4 bar, and reacting the intermediate C in the presence of 4-8% w/w Wilkinson's catalyst at 30° C. for 8 hours to give crude selamectin D, which is then recrystallized with toluene to give pure selamectin D.

2. The synthesis method according to claim 1, wherein the temperature for the desugarization and oximation reaction in step (2) is 30-32° C.

3. The synthesis method according to claim 1, wherein the intermediate C and the mixed solvent in step (2) are mixed at a weight ratio of 1:2 to 1:4, and the water to acetonitrile in the mixed solvent are used at a weight ratio of 1:2 to 1:2.

4. The synthesis method according to claim 3, wherein the weight ratio of the intermediate C to the mixed solvent is 1:3, and the weight ratio of water to acetonitrile in the mixed solvent is 1:2.

5. The synthesis method according to claim 1, in step (2), further comprising recrystallizing the yellow filter cake by adding the mixed solvent of acetonitrile and water to the yellow filter cake, keeping the temperature at 40-80° C. and stirring for 2 hours, cooling and precipitating, carrying out suction filtration, washing the solid with the mixed solvent until white, and drying.

6. The synthesis method according to claim 1, wherein in step (3), the crude selamectin D is recrystallized with toluene at a weight ratio of 1:2 to 1:5.

7. The synthesis method according to claim 6, wherein the weight ratio of the crude selamectin D to toluene is 1:4.

8. The synthesis method according to claim 1, in step (3), further comprising recrystallizing crude selamectin D by adding toluene to the crude selamectin D, dissolving by heating, keeping the temperature at 40-80° C. and stirring for 2 hours, cooling and precipitating, carrying out suction filtration, washing the solid with toluene until white, and drying.

* * * * *